US011178859B2

(12) United States Patent
Ciobanu et al.

(10) Patent No.: US 11,178,859 B2
(45) Date of Patent: Nov. 23, 2021

(54) BIOMARKERS FOR RESISTANCE TO PORCINE CIRCOVIRUS 2 ASSOCIATED DISEASE

(71) Applicant: The Board of Regents of the University of Nebraska, Lincoln, NE (US)

(72) Inventors: Daniel Constantin Ciobanu, Lincoln, NE (US); Lianna Rayne Walker, Lincoln, NE (US); Taylor Benjamin Engle, Lincoln, NE (US); Hiep Vu, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 16/149,059

(22) Filed: Oct. 1, 2018

(65) Prior Publication Data

US 2019/0098880 A1  Apr. 4, 2019

Related U.S. Application Data

(60) Provisional application No. 62/610,812, filed on Dec. 27, 2017, provisional application No. 62/565,740, filed on Sep. 29, 2017.

(51) Int. Cl.
*A01K 67/027* (2006.01)
*C12N 15/85* (2006.01)

(52) U.S. Cl.
CPC ...... *A01K 67/0275* (2013.01); *C12N 15/8509* (2013.01); *A01K 2217/05* (2013.01); *A01K 2217/07* (2013.01); *A01K 2227/108* (2013.01); *A01K 2267/02* (2013.01); *C12N 2310/20* (2017.05)

(58) Field of Classification Search
CPC .................................................. A01K 67/0275
See application file for complete search history.

(56) References Cited

PUBLICATIONS

Bi et al. (2016, Scientific Reports, vol. 6, pp. 1-12) (Year: 2016).*
Merck Veterinary Manual on Porcine Circovirus Diseases (Year: 2015).*
Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Buta et al. (2013, Stem Cell Res., vol. 11, pp. 552-562) (Year: 2013).*
Butler et al. (2015, International J. Surgery, vol. 23, pp. 217-222) (Year: 2015).*
Carey et al. (2019, BMC Biotechnology, vol. 19, pp. 1-8) (Year: 2019).*
Sato et al. (2019, Recent Advance in Genome Editing-Based Modification in Pigs, Intechopen, pp. 1-55) (Year: 2019).*

* cited by examiner

*Primary Examiner* — Thaian N. Ton
*Assistant Examiner* — David A Montanari
(74) *Attorney, Agent, or Firm* — Tracey S. Truitt; Armstrong Teasdale LLP

(57) ABSTRACT

The present disclosure provides compositions and methods for increasing resistance to PCV2 infection in pigs. The increased resistance may be the result of siRNA or genetic modification through CRISPR or a vectored virus targeting SNPs that are resistant to PCV2 infection.

6 Claims, 8 Drawing Sheets

Specification includes a Sequence Listing.

SEQUENCE LISTING

<160> NUMBER OF SEQ ID NOS: 8

<210> SEQ ID NO 1
<211> LENGTH: 21
<212> TYPE: RNA
<213> ORGANISM: Artificial Sequence

```
<220> FEATURE:
<223> OTHER INFORMATION: siRNA oligomer sense strand

<400> SEQUENCE: 1
cuacaaggcc ggaguggauu u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA oligomer antisense strand

<400> SEQUENCE: 2
auccacuccg gccuuguagu u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA oligomer sense strand

<400> SEQUENCE: 3
ccacaagucc ggagagcagu u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA oligomer antisense strand

<400> SEQUENCE: 4
cugcucuccg gacuuguggu u                                              21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agaagggaga gacagcacca                                                20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
caccagcaca tcttccacct                                                20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
acggcgacaa tggagagcgg                                                20
```

```
<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gggaaacaag aggggccagc a                                              21
```

BIOMARKERS FOR RESISTANCE TO PORCINE CIRCOVIRUS 2 ASSOCIATED DISEASE

STATEMENT REGARDING FEDERALLY SPONSORED RESEARCH OR DEVELOPMENT

This invention was made with government support under 2014-36100-06031, 2015-36100-06031, 2016-36100-06031, NA/NI17AHDRXXXXG037, and 2017-67015-26634 awarded by the United States Department of Agriculture, National Institute of Food and Agriculture. The government has certain rights in the invention.

BACKGROUND

Porcine Circovirus 2 (PCV2) is a member of the Circoviridae family and the smallest virus known to be able to infect mammalian cells. Despite its small size, this single-stranded circular DNA virus has been identified as the causative source of a set of systemic disorders known as Porcine Circovirus Associated Diseases (PCVAD), including Post-Weaning Multi-systemic Wasting Syndrome (PMWS). PMWS has been characterized by severe weight loss, respiratory and enteritic conditions that can lead to mortality. Other symptoms associated with PCVAD include nephritis, dermatitis, reproductive failure, interstitial pneumonia, and lymphoid depletion. PCV2 infection can be detected in all domestic populations of pigs, but most infections are subclinical and only a subset of pigs that experience various triggering factors develop clinical disease. The frequency of subclinical infection, combined with environmental resilience of the virus, has enabled PCV2 to spread worldwide and persist undetected for generations. For example, the first documented PMWS outbreak occurred in 1991, but PCV2 was identified in archival semen samples collected in the early 1970s. Current PCV2 isolates display consistent variation in a 9 bp region of the capsid gene, associated with increased virulence in experimental infection of gnotobiotic pigs, compared to archival PCV2 isolates, indicating viral genetic variation associated with virulence.

Anecdotal field data and initial experimental evidence described differences between breeds in both incidence and severity of PCVAD, supporting the role for host genetic variation in the pathogenesis and etiology of the disease.

What is needed is a method to determine a pig's susceptibility to infection by PCV2 What is further needed is a method for selecting pigs for breeding based on their susceptibility to infection by PCV2. What is still further needed is a method of reducing the susceptibility of a pig to infection by PCV2. What is also needed is a method of genetically modifying a pig such that it is not susceptible to infection by PCV2. What is further needed is a composition for reducing the susceptibility of a pig to infection by PCV2. What is further needed is a method of making and administering a composition for reducing the susceptibility of a pig to infection by PCV2. What is finally needed are compositions and methods for reducing the incidence and/or severity of PCVAD in pigs.

SUMMARY OF THE DISCLOSURE

The present disclosure overcomes the problems inherent in the art.

In one aspect, the present disclosure provides a method to determine a pig's resistance to infection by PCV2 In general, the method comprises the steps of assaying the genome of a pig; and determining the presence of at least one SNP associated with resistance to PCV2 infection. In some forms, the SNP is located on *Sus scrofa* chromosome 7 (SSC7) near Swine Leukocyte Antigen II (SLAII) and SSC12 and any combination thereof. In some forms, the SNP is located upstream of the transcription start site for BIRC5, SOCS3, and SYNGR2. In some forms, the SNP is ALGA0110477, ALGA0039682, ALGA0039710, or is located in the BIRC5, SOCS3, or SYNGR2 genes. In some forms, the SNP is SYNGR2 p.Arg63Cys, BIRC5 g.-343delA, or a combination thereof. In some forms, the presence of the SNP indicates resistance to infection by PCV and a subsequent reduction in the incidence of and/or severity of signs of infection caused by or associated with infection from PCV2 in a pig. Preferably, the resistance to PCV2 infection provides complete protection against all signs of infection. In other forms, the incidence and/or severity are decreased by at least 10%, 20%, 30%, 40%, 50%, 60%, 70%, 80%, 90%, 95%, or more in comparison to a pig that does not have the SNP or that does not have the corresponding region occupied by the SNP deleted, blocked, or silenced.

In another aspect, the present disclosure provides a method for selecting pigs for breeding based on their resistance to infection by PCV2. In general, the method comprises the steps of assaying the genome of a pig; determining the presence of at least one SNP associated with resistance to PCV2 infection, and selecting pigs for breeding that have at least one SNP associated with resistance to infection by PCV2. In some forms, the SNP is located on SSC7, near SLAII and SSC12 and any combination thereof. In some forms, the SNP is located upstream of the transcription start site for BIRC5, SOCS3, and SYNGR2. In some forms, the SNP is ALGA0110477, ALGA0039682, ALGA0039710, or is located in the BIRC5, SOCS3, or SYNGR2 genes. In some forms, the SNP is SYNGR2 p.Arg63Cys, BIRC5 g.-343delA, or a combination thereof.

In another aspect, the present disclosure provides a composition and method of administering the composition for reducing the susceptibility of a pig to infection by PCV2. In some forms, the composition knocks down SYNGR2 mRNA. In some forms, the composition includes siRNA. In some forms, the composition includes at least one sequence selected from the group consisting of sequences having at least 85%, 90%, 91%, 92%, 93%, 94%, 95%, 96%, 97%, 98%, 99% or 99.5% sequence identity to a sequence selected from the group consisting of SEQ ID NOS. 1-4, and any combination thereof. In general, the method comprises the steps of administering a composition that enhances resistance to infection by PCV2 to an animal, preferably a pig. In some forms, the administration includes a member of the group consisting of cationic nanoparticles, lipids, liposomes, antibody (Ab)-fusion molecules such as Ab-protamine and Ab-poly-arginine, as well as cholesterol- and aptamer-conjugated siRNAs. In some forms, the composition is administered systemically. In some forms, the systemic administration is via infusion or injection, or is administered intranasally, orally, or transdermally. In some forms, the administration of the composition increases resistance to infection by PCV and provides a subsequent reduction in the incidence of and/or severity of signs of infection caused by or associated with infection from PCV2 in a pig. Preferably, the resistance to PCV2 infection provides complete protection against all signs of infection. In other forms, the incidence and/or severity are decreased by at least 10%, 20%, 30%, 40%, 50%, 60%, 70%, 80%, 90%, 95%, or more in comparison to a pig that does not have SYNGR2 knocked down. In some forms, the composition blocks the region corresponding to at least one SNP identified herein for pigs that do not have the SNP. "Region corresponding to at least one SNP identified herein" refers to the same genomic region that the SNP occupies in pigs. For example, in the case of p.Arg63Cys, one potential example of the region corresponding to this SNP would be p.Arg63Arg and the composition would block or silence this region.

In another aspect, the present disclosure provides a method of genetically modifying a pig to reduce or eliminate susceptibility to infection by PCV2. In general, the method comprises the steps of using CRISPR or a vectored virus to genetically modify a pig. In some forms, the genetic modification is accomplished through gene editing. In some forms, the gene editing is performed using CRISPR-Cas9. In some forms, the genetically modified region is located near SSC7, SSC12, SLAII, and any combination thereof. In some forms, the genetically modified region is located upstream of the transcription start site for BIRC5, SOCS3, and SYNGR2. In some forms, the genetically modified region is ALGA0110477, ALGA0039682, ALGA0039710, or is located in the BIRC5, SOCS3, or SYNGR2 genes. In some forms, the genetic modification is SYNGR2 p.Arg63Cys, BIRC5 g.-343delA, or a combination thereof. In some forms, the genetic modification edits the sequence in a pig without a SNP that is associated with resistance to PCV2 infection such that it corresponds to or is identical with a SNP that is associated with resistance to PCV2 infection. In some forms, editing the genome to include a SNP associated with resistance to PCV2 infection increases resistance to infection by PCV and a subsequent reduction in the incidence of and/or severity of signs of infection caused by or associated with infection from PCV2 in a pig. Preferably, the resistance to PCV2 infection provides complete protection against all signs (clinical and/or histopathological) of infection. In other forms, the incidence and/or severity after such editing are decreased by at least 10%, 20%, 30%, 40%, 50%, 60%, 70%, 80%, 90%, 95%, or more in comparison to a pig that does not have the SNP or that does not have the corresponding region occupied by the SNP deleted, blocked, or silenced.

In another aspect, the present disclosure provides a composition and method for reducing the susceptibility of a pig to infection by PCV2. In general, the composition knocks down mRNA of a region associated with susceptibility to infection by PCV2. In some forms, the region is located on SSC7, near SLAII and SSC12, and any combination thereof. In some forms, the region is located upstream of the transcription start site for BIRC5, SOCS3, and SYNGR2. In some forms, the region is ALGA0110477, ALGA0039682, ALGA0039710, or is located in the BIRC5, SOCS3, or SYNGR2 genes. In some forms, the region is SYNGR2 p.Arg63Cys, BIRC5 g.-343delA, or a combination thereof. In some forms, the composition includes siRNA. In some forms, the sequence of the siRNA is selected from the group consisting of SEQ ID NOS: 1-4. In some forms, the composition includes at least one sequence selected from the group consisting of sequences having at least 85%, 90%, 91%, 92%, 93%, 94%, 95%, 96%, 97%, 98%, 99% or 99.5% sequence identity to a sequence selected from the group consisting of SEQ ID NOS. 1-4, and any combination thereof. In general, the method comprises the steps of administering a composition that enhances resistance to infection by PCV2 to an animal, preferably a pig. In some forms, the composition is administered via injection, intranasally, orally, or transdermally. In some forms, the administration of the composition increases resistance to infection by PCV and provides a subsequent reduction in the incidence of and/or severity of signs of infection caused by or associated with infection from PCV2 in a pig. Preferably, the resistance to PCV2 infection provides complete protection against all signs of infection. In other forms, the incidence and/or severity are decreased by at least 10%, 20%, 30%, 40%, 50%, 60%, 70%, 80%, 90%, 95%, or more in comparison to a pig that does not have SYNGR2 knocked down. In some forms, the composition blocks the region corresponding to at least one SNP identified herein for pigs that do not have the SNP. "Region corresponding to at least one SNP identified herein" refers to the same genomic region that the SNP occupies in pigs. For example, in the case of p.Arg63Cys, one potential example of the region corresponding to this SNP would be p.Arg63Arg and the composition would block or silence this region.

In another aspect, the present disclosure provides a method of making and administering a composition for reducing the susceptibility of a pig to infection by PCV2. In general, compositions as described herein are prepared and administered using conventional methods. Compositions may include one or more pharmaceutically-acceptable carriers, one or more adjuvants, or any combination thereof. As used herein, "a pharmaceutically-acceptable carrier" includes any and all solvents, dispersion media, coatings, stabilizing agents, diluents, preservatives, antibacterial and antifungal agents, isotonic agents, adsorption delaying agents, and the like. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). JohnWiley and Sons, NY, pp 51-94 (1995) and Todd et al., Vaccine 15:564-570 (1997). A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g.

vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

In another aspect, the present disclosure provides compositions and methods for reducing the incidence and/or severity of PCVAD in pigs. In general, the composition knocks down mRNA of a region associated with susceptibility to infection by PCV2. In some forms, the region is located on SSC7, near SLAII and SSC12 and any combination thereof. In some forms, the region is located upstream of the transcription start site for BIRC5, SOCS3, and SYNGR2. In some forms, the region is ALGA0110477, ALGA0039682, ALGA0039710, or is located in the BIRC5, SOCS3, or SYNGR2 genes. In some forms, the region is SYNGR2 p.Arg63Cys, BIRC5 g.-343delA, or a combination thereof. In some forms, the method for knocking down gene expression in vivo could be by gene editing using siRNA or methods such as CRISPR-Cas9. In some forms, the sequence of the siRNA is selected from the group consisting of SEQ ID NOS: 1-4 or a sequence having at least 85%, 90%, 91%, 92%, 93%, 94%, 95%, 96%, 97%, 98%, 99% sequence identity with any one of SEQ ID NOS. 1-4. In general, the methods will administer the composition though any conventional administration modes including injection, topical, and systemic, and any combination thereof. When using methods employing CRISPR-Cas9, the targeted areas for gene editing are the same as those for siRNA.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

In a previous genome-wide association study, it was found that host genetics influenced PCV2 titer and accounted for an important proportion of the phenotypic variation (~45%) for viral load (McKnite et al, 2014). In this study, two datasets of pigs experimentally infected with PCV2 (McKnite et al., 2014; Engle et al., 2015) and an in vitro validation model to elucidate the role of host genetics in disease progression were integrated by identifying genes and genetic variants that influence PCV2 susceptibility.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1:
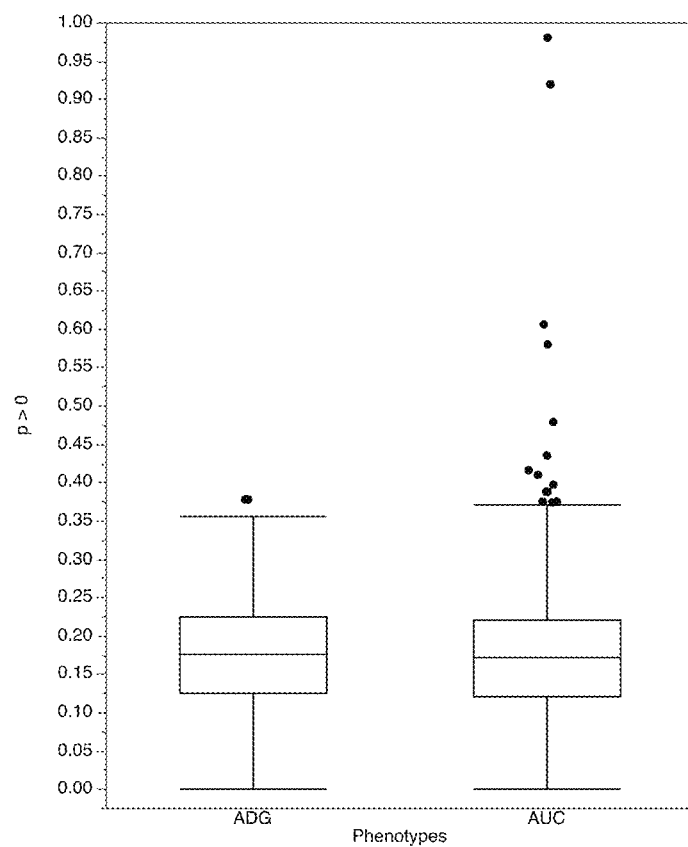
FIG. 1 is an illustration of the probability of a 1 Mb window to have an effect above the average effect of the genome-wide 1 Mb windows estimated using BayesB on overall Average Daily Gain (ADG) and PCV2 viral load (AUC). The genetic variance for PCV2 viral load explained by the top two 1 Mb windows that included ALGA0039682 (SSC7) and ALGA0110477 (SSC12) have effects above the 1 Mb average effect across 1 Mb windows (P>0.90)

The following detailed description and examples set forth preferred materials and procedures used in accordance with the present disclosure. It is to be understood, however, that this description and these examples are provided by way of illustration only, and nothing therein shall be deemed to be a limitation upon the overall scope of the present disclosure.

Example 1

Materials and Methods
Experimental Design: Animals, Diets, and Housing

The experimental PCV2 challenge was conducted in nine batches that varied in size from 81 to 141 pigs, with a total of 974 pigs. The genetic makeup of this resource population consisted of crossbred pigs produced by 14 genetic lines generated by seven genetic programs. The dams of the experimental pigs had been vaccinated for PCVAD at 3 weeks of age with a single dose of Ingelvac CircoFLEX vaccine (Boehringer Ingelheim). The suppliers of the pigs also have vaccination programs for Porcine parvovirus, *Erysipelothrix rhusiopathiae, Clostridium perfringens, Leptospirosis* and *Colibacillosis* and tested negative for Porcine Reproductive and Respiratory Syndrome Virus (PRRSV). Prior to experimental infection, the pigs tested negative for presence of PCV2 in peripheral blood by real time quantitative PCR (qPCR) and had a sample/positive ratio (S/P) lower than 0.4 for IgM and 0.3 for passive IgG, the PCV2- specific antibodies. As described in INGEZIM Circovirus Enzyme-linked immunosorbent assay protocols (ELISA; Ingenasa), these S/P thresholds provide an indication if the pigs are actively infected (IgM) or were previously exposed to PCV2 (IgG)(Ingenasa). Following infection, experimental pigs were examined daily for clinical signs of disease; weights and blood samples were collected at 0, 7, 14, 21 and 28 days post infection (dpi). Details of the experimental procedures, phenotypic and sample collection are described in Engle et al. (2014) and McKnite et al. (2014), the contents and teaching of which are hereby incorporated by reference.

A validation dataset consisting of a group of 71 pigs of all three SYNGR2 p.Arg63Cys genotypes infected with the same PCV2b strain at 5 weeks of age was generated using the same experimental conditions. A group of 40 pigs (SYNGR2 p.63Arg/63Cys and 63Arg/63Arg) vaccinated for PCV2 at 3 weeks of age were used as controls. The vaccinated pigs were housed in the same room with the experimentally infected pigs, but in different pens.

PCV2b Isolate and Experimental Infection

The PCV2b strain (UNL2014001) used for the experimental infection was obtained from a pig with symptoms characteristic to Post-weaning Multisystemic Wasting Syndrome (PMWS), which is the most common PCVAD syndrome. There are many isolates/strains of PCV2, usually clustered in subgroups. Currently, PCV2 is divided into three subgroups denoted PCV2a, PCV2b, and PCV2c, with PCV2a and PCV2b found worldwide. The existence of two more groups, PCV2d and PCV2e, has been proposed based on isolates from China. There are hundreds of sequences available. Of course, these multiple strains and isolates are readily available and any of those strains or isolates could also be used in a similar manner as demonstrated herein. The strain was sequenced (accession KP016747.1) using dye terminators and the sequence compared to PCV2 strains available in GenBank (Engle et al., 2014, the teachings and contents of which are hereby incorporated by reference). The strain was cultured in swine testicular cell lines as described (McKnite et al., 2014) (incorporated by reference herein). At an average of 36 days, all the pigs were inoculated with the UNL2014001 PCV2b strain with a titer of $10^{4.0}$ 50% tissue culture infection dose (TCID50) intranasally and intramuscularly.

Serologic Profile: Quantification of Viral DNA and PCV2-Specific Antibodies

PCV2 specific antibodies, IgM and IgG, were profiled weekly from serum using ELISA (Ingenasa) as described in McKnite et al. (2014) (incorporated by reference herein). Estimates of the number of PCV2b copies, or viremia, were performed using viral genomic DNA isolated by QIAamp DNA Minikit (Qiagen) and quantified by qPCR using TaqMan Master Mix and ABI 7900 Real Time PCR System (Thermo Scientific). The viral load for each pig during the entire challenge was represented as area under the curve (AUC) based on an algorithm that takes into account viral levels observed at each time point following infection (0, 7, 14, 21, and 28 dpi) fitting a smooth curve over the 28 days and summing the areas in 0.01 time increments (Boddicker et al., 2012) (incorporated by reference herein).

RNA-Seq and Gene Expression Profiling

In order to profile transcriptome changes and sequence variation related to PCV2 infection, peripheral blood samples collected from the validation group of pigs that exhibited high ($N_{TT}$=6) and low ($N_{CC}$=5) viremic genotypes for ALGA0110477 at 0, 7 and 14 dpi were subjected to RNA sequencing. RNA was extracted from peripheral blood collected in Tempus tubes using the Tempus Spin RNA Isolation Reagent Kit (Thermo Scientific). RNA samples were sequenced using Ion Proton technology as described in the manufacturer protocol (Thermo Fisher Scientific Inc.). The adaptor-free sequencing reads were trimmed and filtered using Trim galore (version 0.4; Krueger, 2015) (incorporated by reference herein) with low-quality bases in the 5' end being removed and nucleotides with quality call less than 22 being trimmed off from the 3' end. The filtered reads were initially aligned to the SSC12 genome scaffold (19 Mb) using the two-step alignment approach used for Ion Proton transcriptome data that includes both Tophat and local-Bowtie (Blair et al., 2014) (incorporated by reference herein). The reads were later also aligned to the new pig assembly Sscrofa 11.1. The number of reads mapped to each gene in the annotated QTL region was obtained using HTSeq (version 0.6.1p1; Anders, 2014) (incorporated by reference herein).

Expression of the candidate genes SOCS3, BIRC5 and SYNGR2 across time points following PCV2 infection was quantified using TaqMan Master Mix and CFX384 Real Time PCR. The qPCR assays were designed using IDT Realtime PCR Tool software (available at the idt website) and the sequences generated based on RNA-seq alignments. RNA was extracted from peripheral blood samples collected in Tempus tubes from a subset of pigs representing all genotypes from the validation data set that displayed extreme viral load (high vs low)(n=40) from 0 to 21 dpi using the Tempus Spin RNA Isolation Reagent Kit (Thermo Scientific). Complementary DNA (cDNA) was obtained using a mix of random hexamers and poly dT primers using First strand cDNA Synthesis Kit (GE Healthcare Bio-Sciences). Expression of ribosomal protein L32 (Rpl32) gene was used for normalization. Mean normalized expression (MNE) values were calculated based on cycle crossing thresholds (CT) obtained for the technical triplicates taking qPCR efficiencies into account (Simon, 2002). MNE values for ALGA0110477, SYNGR2 p.Arg63Cys or BIRC5 g.-343delA genotypes and time point following infection were log 10 transformed and compared by a t-test.

Novel Assembly of the Proximal End of SSC12

Inverse PCR (iPCR), using four (AciI, AluI, HaeIII, HpaII, RsaII) and six cutter (EcoRI, HaeII, HincII, HindIII, KpnI, MfeI, MspA11) restriction enzymes (New England Biolabs), T4 DNA ligase (New England Biolabs) and nested PCR using AmpliTaq Gold 360 DNA polymerase (Thermo Scientific), was employed to expand the genomic DNA sequence surrounding the short ALGA0110477 sequence, a SNP previously unmapped on the Sscrofa 10.2 reference genome. A genomic scaffold (19 Mb) of the proximal end of SSC12 was constructed based on Pacific Biosciences sequencing reads (Smith et al., 2016) (incorporated by reference herein). The position of the extended ALGA0110477 sequence and all SSC12 mapped and unmapped SNPs were determined on the genomic scaffold using BLAT. Annotation of the QTL region on the SSC12 scaffold was based on RNA-seq alignments and BLAST but also using Ab initio approaches such as GenScan (Burge et al., 1997, 1998) (incorporated by reference herein) in combination with pBLAST.

Host Genetic Profile: DNA Isolation, Sequencing, Polymorphism Discovery and Genotyping.

The DNA was isolated from ear and tail tissue clips using DNeasy or Puregene blood and tissue kits (Qiagen). The experimental animals were genotyped using either the first or second generation of the Porcine SNP60 BeadArray (Illumina) that contain 62,183 and 61,565 SNPs, respectively. Most of the common SNPs present in both BeadArray versions (91.6%, 61,177) were mapped on Sscrofa 10.2 porcine reference genome assembly. An additional 7.2% of the previously unmapped SNPs, including ALGA0110477, were mapped on Sscrofa 11.1.

The broad position of the unmapped SNPs on the original Sscrofa 10.2, such as ALGA0110477, was predicted by linkage disequilibrium estimates ($r^2$) with the mapped SNPs using "Linkage disequilibrium" option from GenSel software package (Fernando and Garrick, 2009) (incorporated by reference herein). The low quality DNA samples and SNP assays were removed by using as thresholds a minimum GenCall genotype quality score of 0.40 and a genotyping call rate of 0.80 (Tart et al., 2013) (incorporated by reference herein).

Targeted DNA sequencing of candidate genes in the SSC12 QTL region including SOCS3, BIRC5 and SYNGR2 and their 2-4 kb region upstream of the transcription start sites (TSS) was performed using dye terminators and ABI PRISM 3100 Genetic Analyzer (Thermo Scientific) on high and low viremic samples. Discovery and validation of the polymorphisms detected by RNA-seq was based on alignment of DNA sequences using Sequencher software (Gene Codes). Potential impact of the polymorphisms located in the proximal promoter on important regulatory motifs was evaluated using FIMO (version 4.11.3, Grant et al., 2011) and the JASPAR transcription profile database (version 2016).

Genotyping of polymorphisms located in the transcribed regions and proximal promoters of SOCS3, BIRC5, SYNGR2, THAI, TMC6 and TMC8 was performed by multiplex assays using Sequenom MassARRAY platform and Sequenom iPLEX chemistry based on the manufacturer protocols (Sequenom, San Diego, Calif.). Haplotyping the swine leukocyte antigen class II (SLAII) was based on the reference haplotype information obtained from the Immuno Polymorphism Database (located on the web at ebi.ac.uk/ipd/mhc) and sequencing DQB1 gene in experimental samples (Engle et al., 2015) (incorporated by reference herein).

RNA was extracted from peripheral blood samples collected in Tempus tubes from pigs that displayed extreme viral load (high vs low) using the Tempus Spin RNA Isolation Reagent Kit (Thermo Scientific). Expression of BIRC5 and SYNGR2 across time points following PCV2 infection was quantified using TaqMan Master Mix and CFX384 Real Time PCR Detection System (BioRad).

Genome-Wide Associations

The proportion of phenotypic variance explained by host genetics for PCV2-viremia, PCV2-specific antibodies (IgM and IgG) and average daily gain (ADGi) during experimental infection was estimated based on Porcine SNP60 BeadArray genotypes using a BayesB model (Kizilkaya et al., 2010) (incorporated by reference herein) and GenSel software (Fernando and Garrick, 2009) (incorporated by reference herein). The statistical model included litter, pen and batch as class variables and passive IgG and age at infection as covariates. Bayesian analyses were based on π equal to 0.99 that assumed a prior probability of 1% of the SNPs having a non-zero effect. The Markov chain included 40,000 samples with the first 1,000 being removed as burn-in. Markov chain was set to use every 40th sample to estimate posterior distribution for the genetic variance explained by each 1 Mb window of the reference genome. This distribution was used to estimate the probabilities of each 1 Mb window having a variance greater than 0 or greater than the average variance explained by each 1 Mb window as described in McKnite et al. (2014) (incorporated by reference herein).

Bayes Interval Mapping (BayesIM) was implemented to derive haplotype effects across the genome on PCVAD-related traits as described in Kachman (2014) (incorporated by reference herein). Briefly, a hidden Markov model was used to generate either 8 or 16 haplotype states based on SNP genotypes (Scheet and Stephens, 2006) (incorporated by reference herein). Phenotypic variation of the targeted traits was analyzed with a hierarchal Bayesian model. QTL were placed every 50 kb across the genome while average haplotype size was set to 500 kb. Genetic variances, haplotype effects, and model frequencies were estimated at each locus. There were 42,000 MCMC samples collected with the first 2,000 used for burn-in. The model included batch, litter and pen as random effects and IgG and age at infection used as covariates. If a locus had an effect, haplotype effects for each cluster were modeled as independent normal random variables.

Associations between the single marker genotypes and phenotypic variation were tested using a linear mixed model fitted by JMP 10.0 (SAS Inst. Inc.) that included marker genotype and batch as fixed effects, litter and pen as random effects while age at infection and IgG were used as covariates. Additive and dominance effects were estimated for each of the targeted DNA polymorphisms. A similar model was used to estimate the interaction between SNPs.

In Vitro PCV2 Infection of PK15 Cells

The porcine kidney cell line (PK15), was grown in DMEM high glucose media supplemented with 10% FBS and 1% Penicillin-Streptomycin (5,000 U/mL). Cells were cultured in 12-well plates (4 cm$^2$) with $5.0 \times 10^5$ cells per well and infected with UNL2014001 PCV2b strain (TCID50=$10^4$) when 80-100% confluent at MOI=0.00025. After 1 hour following infection, cells were washed and fresh media was added (DMEM high glucose and 2% FBS). The cells were incubated at 37° C. with 5% $CO_2$ up to 5 days. Control cells were maintained the same way and mock-inoculated with plain DMEM high glucose media. Supernatants and cells were collected at specific time points and frozen at −80° C. Viral DNA was extracted from supernatants using QIAamp DNA Mini kit (Qiagen). RNA, viral and host DNAs were extracted from PK15 cells using AllPrep DNA/RNA Mini kit (Qiagen). TaqMan Master Mix and CFX384 Real Time PCR Detection System (BioRad) were used for quantification of PCV2 and expression profiling of BIRC5 and SYNGR2 from PK15 cells. Dideoxy sequencing of the cDNA and genomic DNA was used to profile the sequences and to genotype BIRC5 and SYNGR2 variants in PK15 cells.

In Vitro Silencing of SYNGR2 in PK15 Cells

PK15 cells were transfected 24 hours after plating in 12-well plates (4 cm$^2$) with $2.5 \times 10^5$ cells per well when ~80% confluent with two siRNA oligos (siRNA-01: sense 5'-CUACAAGGCCGGAGUGGAUUU-3' (SEQ ID NO. 1), and antisense 5'-AUCCACUCCGGCCUUGUAGUU-3' (SEQ ID NO. 2); siRNA-03: sense 5'-CCACAAGUCCG-GAGAGCAGUU 3'(SEQ ID NO. 3), and antisense, 5'-CUGCUCUCCGGACUUGUGGUU-3'(SEQ ID NO. 4), Dharmacon Research) targeting SYNGR2 mRNA and the AllStars Negative Control siRNA (scramble, Qiagen) at 10 nM and 20 nM concentrations. Transfection was performed using Lipofectamine RNAiMAX transfection reagent (Invitrogen) following the manufacturer's protocol. Cell samples were collected 24, 48, 72, and 96 hours post transfection in PBS using a rubber scraper and centrifuged at 16,000×g for 1 minute to pellet the cells. RNA was extracted using RNAeasy Mini kit (Qiagen). Real Time PCR was used to profile SYNGR2 expression. siRNA oligo 01 (SEQ ID NO. 1) and the AllStars Negative Control siRNA (20 nM) were used for subsequent transfections prior to infection. The siRNA transfected cells were inoculated 24 hr after transfection following the same infection protocol described above.

Results

Two Genomic Loci Influence Host Genetic Effect on PCV2 Infection

Substantial variation in the timing and magnitude of immune response, and in the efficiency of PCV2 replication, was reported in previous studies of experimental infection with PCV2. The present disclosure extends that work by examining the influence of host genetics on the process of infection, based on a combination of the two previous study populations (n=974 F1 crossbred pigs originating from 14 genetic lines) challenged by experimental infection with PCV2 and genotyped with a high-density array (Porcine SNP60 BeadArray, 56,433 SNPs). The population structure provides substantial variation in linkage disequilibrium (LD) decay in order to identify genomic regions that influence the phenotype using a genome-wide association study (GWAS) approach. Key phenotypes included viremia and PCV2-specific antibodies at specific time points, overall viral load across the study, and growth rate as a measure of impact of infection. The proportion of phenotypic variation accounted for by SNP genotypes was limited early in the infection, but increased after the surge in viral replication and associated immune response. Specifically, SNP genotypes explained from 19% of phenotypic variation in PCV2 viremia at 7 days post infection (7 dpi) to 52% at 14 dpi (Table 1). Similarly, SNP genotypes explained 14% and 3% of PCV2-specific IgM and IgG variation at 7 dpi, respectively, but this increased to 60% (IgM) and 44% (IgG) at 21 dpi. Overall, SNP genotypes explained 64% of the variation in viral load calculated across time points. In comparison, the contribution of SNP genotypes to variation in Average Daily Gain (ADG, monitoring growth rate through body weight) during the study period was limited, explaining 16% of the variation in overall ADG with 13% explained at 7 dpi and 7% at both 21 and 28 dpi.

TABLE 1

Proportion of phenotypic variance explained by 56,433 SNPs using Bayes B of PCV2-related traits days post infection (dpi) with PCV2.

| Trait/dpi | 7 | 14 | 21 | 28 | 0-28 |
| --- | --- | --- | --- | --- | --- |
| Viremia | 0.19 | 0.52 | 0.45 | 0.39 | 0.64 |
| IgM | 0.14 | 0.60 | 0.44 | 0.52 | |
| IgG | 0.03 | 0.08 | 0.44 | 0.38 | |
| | 0-7 | 7-14 | 14-21 | 21-28 | 0-28 |
| ADG | 0.13 | 0.11 | 0.07 | 0.07 | 0.16 |

Initial GWAS analysis was based on mapping of SNP probes to the available Sscrofa 10.2 reference genome assembly. The association analysis was performed using a BayesB-based approach where individual SNPs and successive 1 Mb windows of the genome were evaluated for association with phenotypic variation (McKnite et al., 2014) (incorporated by reference herein).

Bayesian regression models fit multiple SNPs in genome-wide associations, assuming that the marker effects result from a mixture of a point mass distribution whereby SNP have null effects and a distribution of non-zero effects (e.g., normal, heavy tailed). Prior assumptions are made relative to the genetic and environmental variances and the proportion of markers that have a null effect on a specific trait of interest. These models are implemented via a Markov Chain Monte Carlo (MCMC) sampling algorithm. The posterior means are averaged over the number of samples from the MCMC chain (Fernando and Garrick, 2013) (incorporated by reference herein). Genome-wide average posterior distribution for the genetic variance was used to estimate the probability of each 1 Mb window having greater than the average genetic variance explained across PCV2-related traits. The analysis identified two windows with greater than average effect associated with both viral replication and immune response phenotypes (Pr>0.90), assumed to represent Quantitative Trait Loci (QTL) (FIG. 1). One window associated with viral load was found on SSC7 in the vicinity of the swine leukocyte antigen complex class II (SLAII) at 28-29 Mb while the other was putatively located near the proximal end of SSC12, at approximately 3-4 Mb. The SNPs associated with the largest genetic variance (ALGA0039682 and ALGA0110477) in each of these two windows explained greater than 94% of the genetic variance explained by their respective windows.

Figure 9:
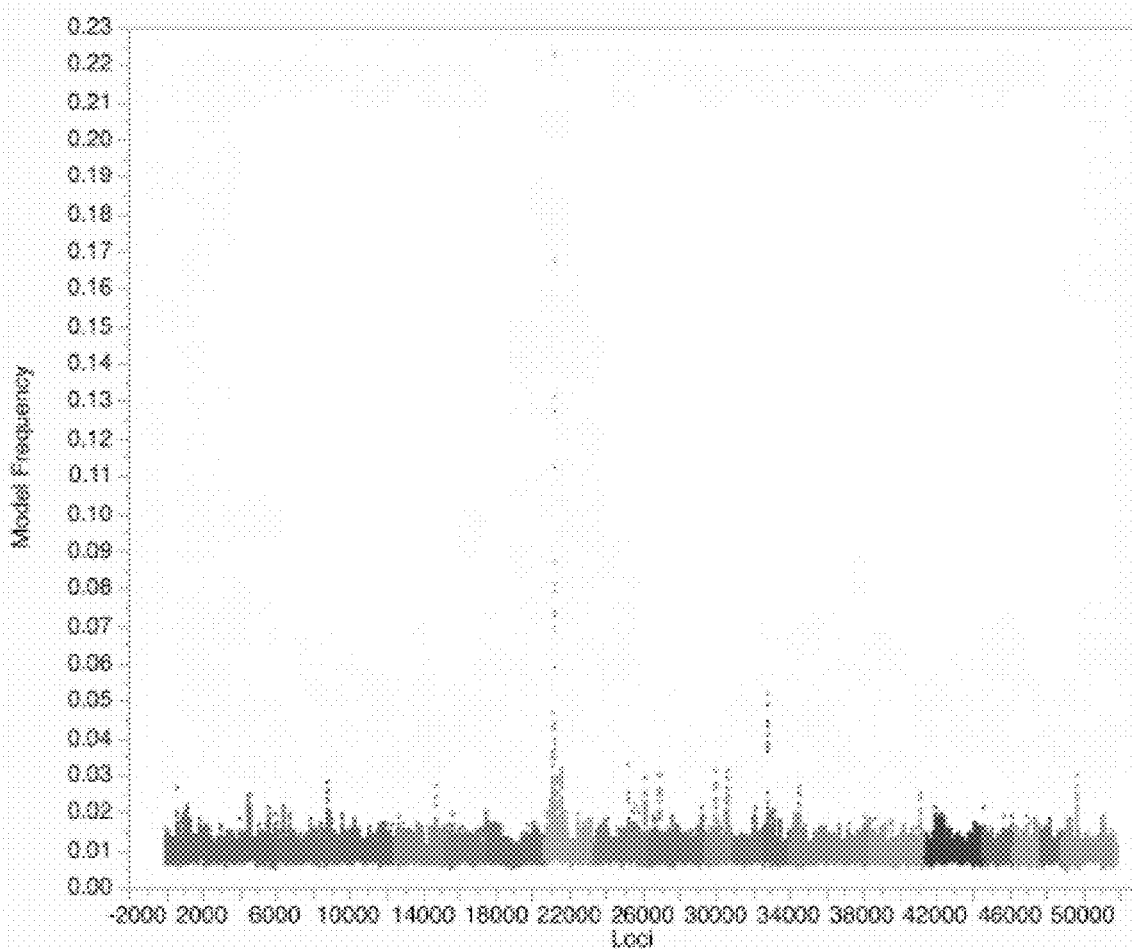
FIG. 9 is an illustration representing genome-wide association between 54,946 SNPs and PCV2b viral load using BayesIM. Marker ALGA0110477 was excluded from the analysis. Each dot represents the model frequency associated with each 50 kb QTL segment. The X-axis represents the position of the 50 kb loci across the swine genome using Sscrofa 10.2 assembly. The Y-axis represents the model frequency of the association between a QTL segment and PCV2 viral load. Alternate colors represent autosomes, from SSC1 to 18.

The SNP (ALGA0110477) associated with the largest effect on viral load explained 11.1% of the genetic variance and 7.4% of the phenotypic variance for PCV2 viral load. However, this SNP was located on an unplaced scaffold in the 10.2 reference assembly. Estimating LD between ALGA0110477 and all other SNPs on the Porcine SNP60 BeadArray provided weak evidence of its location at the proximal end of the SSC12 reference sequence. Specifically, SNPs ALGA0122316, ASGA0089708, and ASGA0090188 had the highest LD estimates with ALGA0110477 ($r^2>0.28$). Interestingly, SNPs in the genomic region encompassing these markers did not show strong evidence of association with viral load despite LD with ALGA0110477. However, a more nuanced analysis fitting haplotypes across the region rather than individual SNP using BayesIM (Kachman, 2014) (incorporated by reference herein) detected an effect in this genomic region (FIG. 9), providing support for the initial discovery that was based only on the ALGA0110477 marker. The unplaced scaffold containing the putative SSC12 marker, ALGA0110477, did not contain any annotated candidate genes that might underlie the observed effects, and the available sequence surrounding the marker only extended for 84 bp. Using inverse PCR (iPCR), we extended the available sequence to 1,252 bp. This extended sequence was used to interrogate contigs from an early version of a long read-based genome assembly of a pig (Smith et al. 2016, accession NPJO00000000), which identified a 19 Mb scaffold that provided precise location and context for ALGA0110477 that was used for identification of candidates genes described below.

Figure 2:
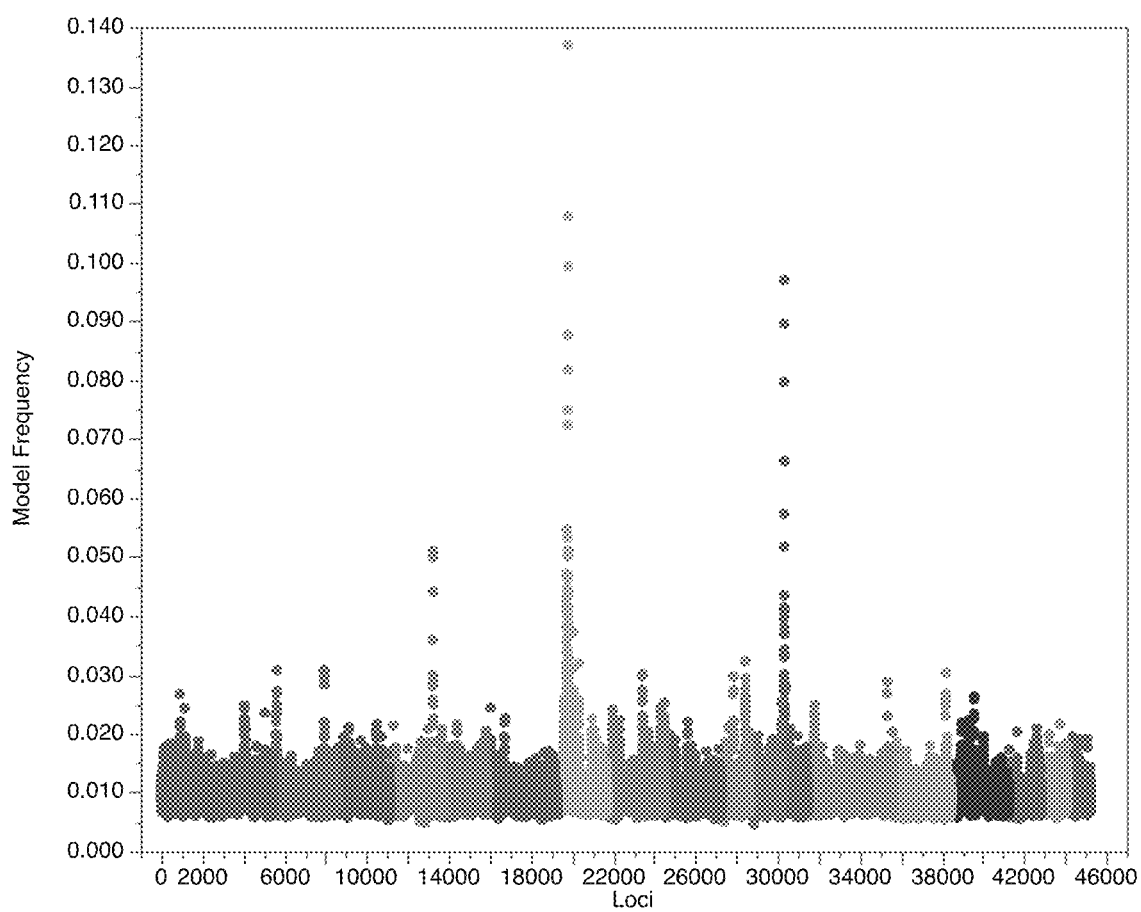
FIG. 2 is an illustration of the genome-wide association between 51,592 SNPs and PCV2b viral load using BayesIM. Each dot represents the model frequency associated with each 50 kb QTL segment. The X-axis represents the position of the 50 kb loci across the swine genome using Sscrofa 11.1 assembly. The Y-axis represents the model frequency of the association between a QTL segment and PCV2 viral load. Alternate colors represent autosomes, from SSC1 to 18.
Figure 6:
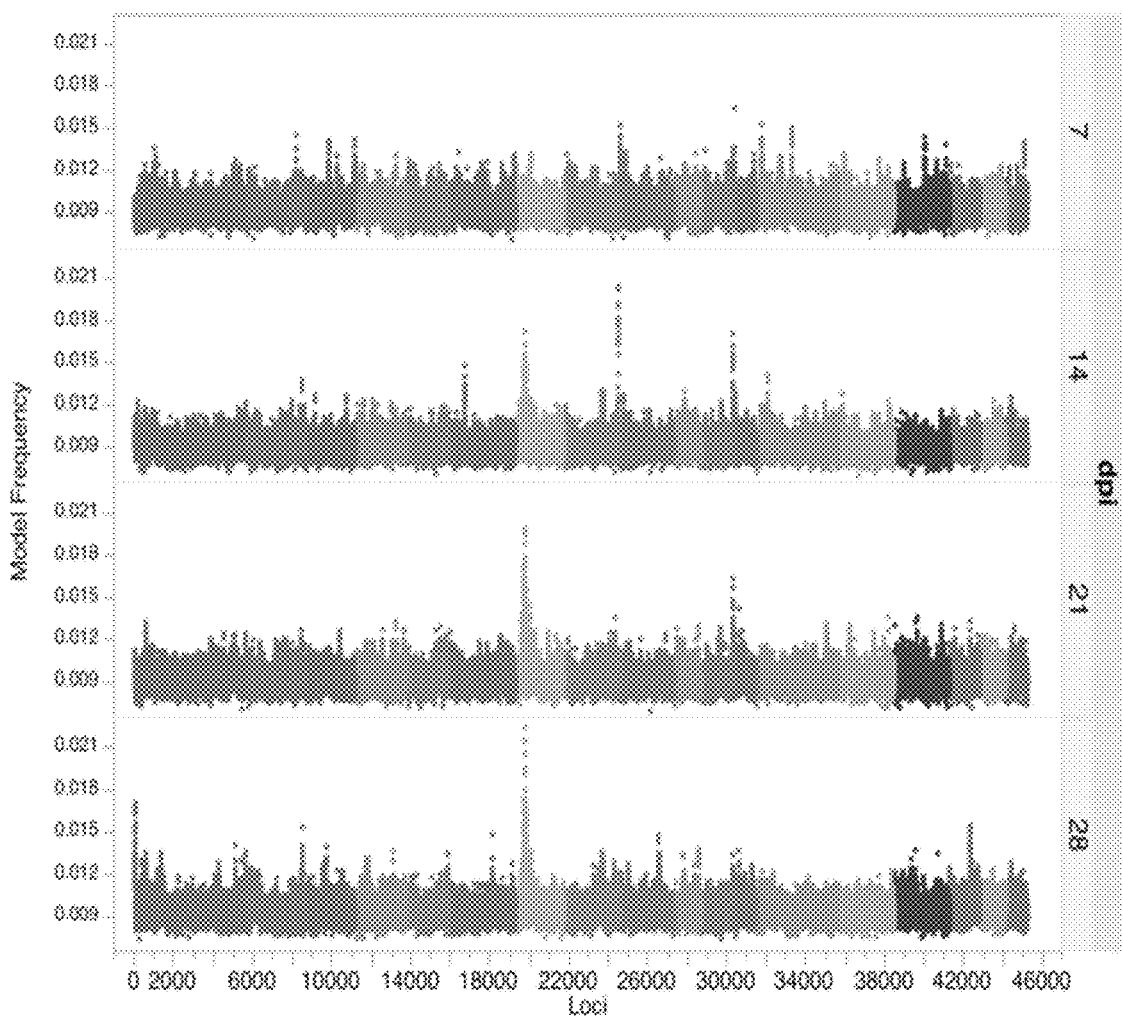
FIG. 6 is an illustration representing genome-wide association between 51,592 SNPs and PCV2 viremia using BayesIM. Each dot represents the model frequency associated with each 50 kb QTL segment. The X-axis represents the position of the 50 kb loci across the swine genome using Sscrofa 11.1 assembly. The Y-axis represents the model frequency of the association between a QTL segment and PCV2 viral load. Alternate colors represent autosomes, from SSC1 to 18.
Figure 7:
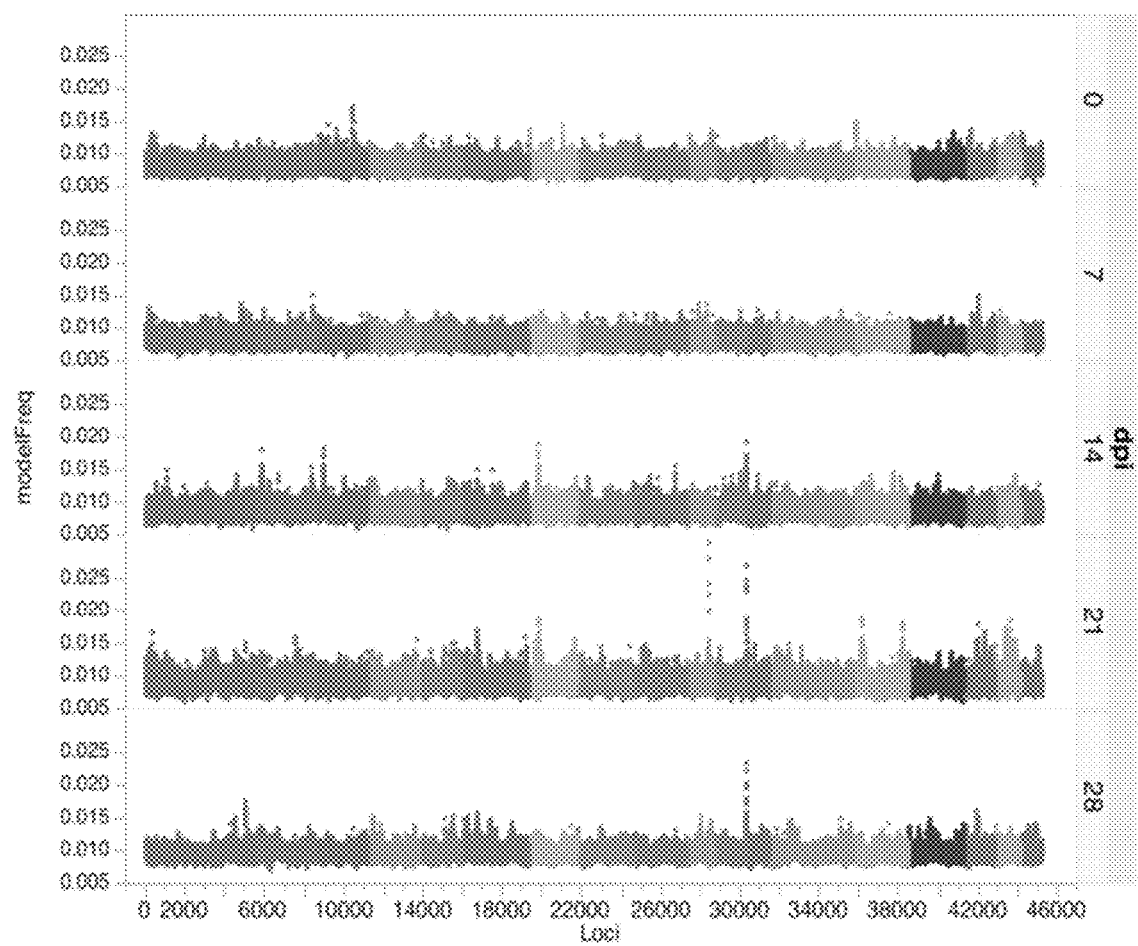
FIG. 7 is a graph representing genome-wide association between 51,592 SNPs and IgM using BayesIM. Each dot represents the model frequency associated with each 50 kb QTL segment. The X-axis represents the position of the 50 kb loci across the swine genome using Sscrofa 11.1 assembly. The Y-axis represents the model frequency of the association between a QTL segment and IgM following PCV2 infection. Alternate colors represent autosomes, from SSC1 to 18.
Figure 8:
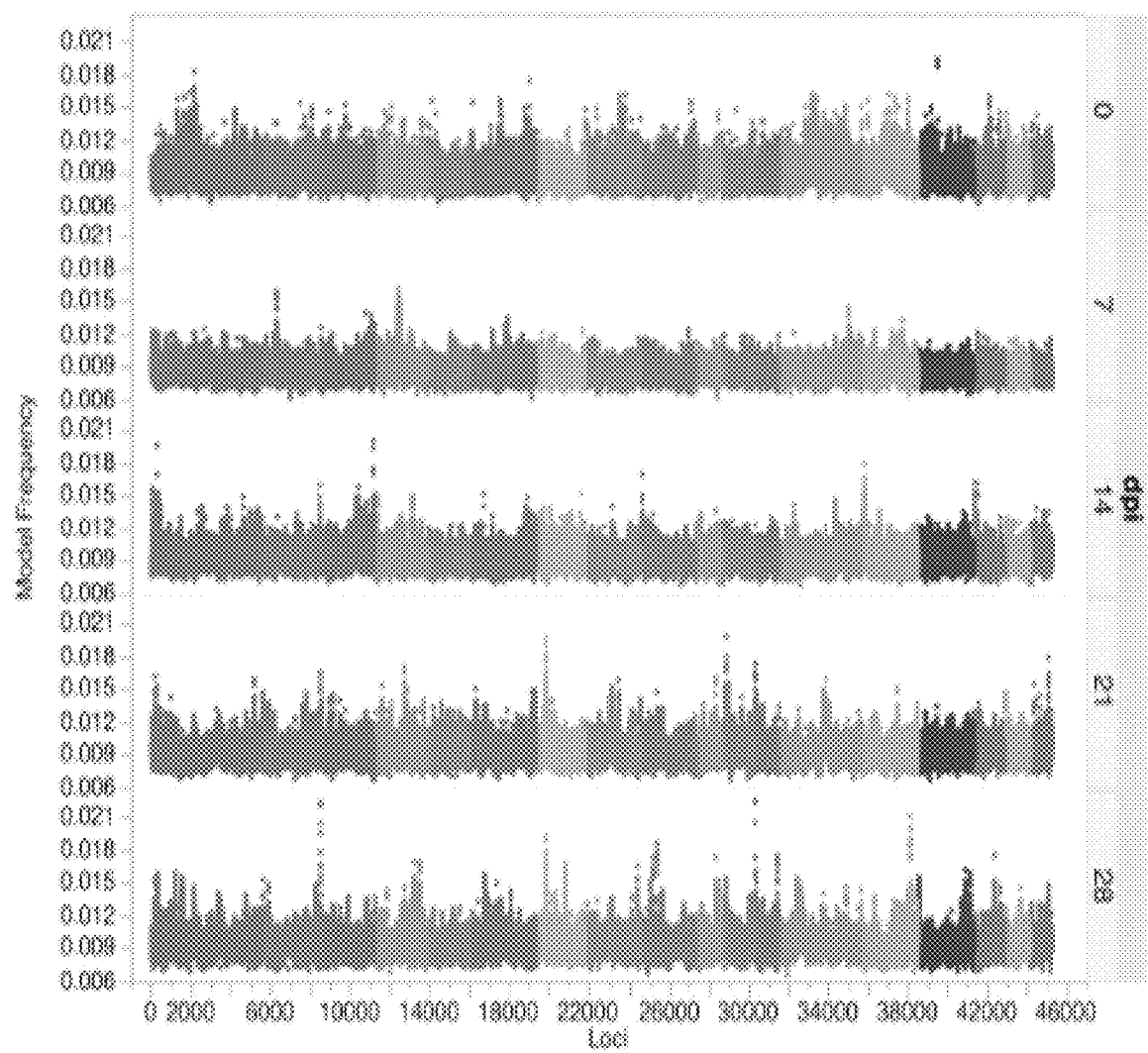
FIG. 8 is an illustration representing genome-wide association between 51,592 SNPs and PCV2-specific IgG using BayesIM. Each dot represents the model frequency associated with each 50 kb QTL segment. The X-axis represents the position of the 50 kb loci across the swine genome using Sscrofa 11.1 assembly. The Y-axis represents the model frequency of the association between a QTL segment and PCV2-specific IgG following PCV2 infection. Alternate colors represent autosomes, from SSC1 to 18.

The recent release of a long read-based improved reference assembly, Sscrofa 11.1 (GenBank accession GCA_000003025), supported more accurate ordering and placement of markers, including ALGA0110477 (SSC12, 3,673,576 bp), and facilitated finer analysis into genomic context with surrounding gene annotation. As a result, an enhanced profiling of the loci associated with PCV2-related phenotypes across time points was possible in order to distinguish host genetics role in innate and adaptive immunity (FIG. 6). One of the outputs of Bayesian analyses is model frequency that provides the proportion of post-burn-in samplings that included a particular SNP covariate in the model. Model frequency can be also used to compare loci effects across multiple traits, despite differences in phenotypic and genetic variances. This analysis based on BayesIM supported the previous result, with the highest model frequency for viral load occurring within the previously identified locations on SSC7 and SSC12 (FIG. 2). These QTLs were consistently observed for other targeted traits, for example viremia. Both SSC7 and SSC12 QTLs had similar model frequencies at 14 dpi, while the QTL on SSC7 showed increasing effect on viremia at 21 and 28 dpi. It should be noted that an additional QTL on the proximal end of SSC8 was detected for viremia at 14 dpi; this QTL had not been observed for viral load, and represented the largest effect for the 14 dpi. The QTLs located on SSC7 and SSC12 were also observed for PCV2-specific antibody variation. Specifically, these QTLs were associated with IgM variation starting at 14 dpi, and with IgG variation starting at 21 dpi (FIGS. 7 and 8), supporting the hypothesis that they represent host variation affecting PCV2 infection including immune response. The presence of PCV2-binding IgM is an indication of active infection, while the presence of IgG represents either previous exposure to PCV2, or anti-PCV2 vaccination.

SLAII Role in PCV2 Replication and Immune Response

One of the genomic regions associated with viral load was located on SSC7, in the vicinity of SLAII locus. The SNPs associated with the largest effects (ALGA0039682 and ALGA0039710, at 28.4 and 28.9 Mb, respectively) are located at the proximal end of SLAII with DRA being the closest gene (29.0 Mb) from the SLAII complex. These two SNPs combined explained 4.4% of the genetic variance for viral load. While the role of SLAII in antigen recognition and immune response in a variety of infectious diseases is well established, highly polymorphic genes and extended LD are the main factors limiting the discovery of functional variants. The SNP ALGA0039710, was associated with the largest effect in viral load in an analysis of a subset of samples (n=307) with extreme phenotypes that included novel SNPs in the QTL region located in genes such as DRA, C2, CFB, NELFE, SKIV2L and the highly diverse antigen recognition domain of DQB1.

Fine Mapping and Annotation of the QTL Region Located at the Proximal End of SSC12

Previous to the release of the annotated Sscrofa 11.1, the un-annotated long-read scaffold to identify the genes surrounding the SSC12 marker ALGA0110477 was used. Ab initio gene prediction (Genscan, Burge and Karlin, 1997) (incorporated by reference herein) and pBLAST combined with RNA-seq of peripheral blood were used for annotation of this QTL region. Thirteen potential genes with an e value>7e$^{-64}$ and a pBLAST score>200 were identified. Five of these genes were found to be expressed in RNA-seq data of peripheral blood from pigs subjected to PCV2. These genes are involved in immune response and cytokine signaling (SOCS3), inhibition of apoptosis and promotion of cell proliferation (BIRC5), membrane trafficking and transport (SYNGR2) and transmembrane ion channels (TMC6 and TMC8). The number of isoforms observed across these genes varied from one (SOCS3) to more than 10 (TMC6).

Figure 3:
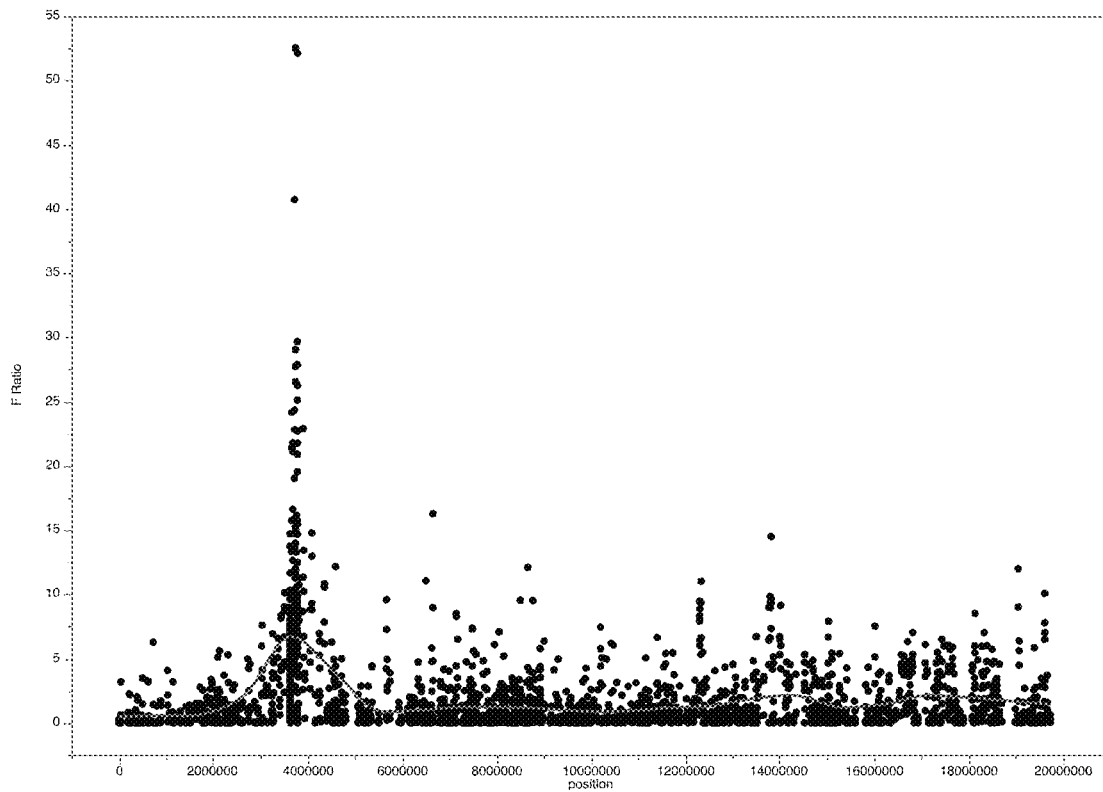
FIG. 3 is an illustration of the association results between the genotypes of the DNA polymorphisms mapped to the 19 Mb scaffold of the proximal end of SSC12 and PCV2 viral load using a Linear Mixed Additive Model. The line represents a smoother with a default λ of 0.05. SYNGR2 p.Arg63Cys and BIRC5 g.-343delA were associated with the largest effects on PCV2 viral load (F-ratio>47, P<0.0001)

RNA-seq analysis of alternate ALGA0110477 homozygotes that expressed extreme viral load following PCV2 challenge uncovered missense (n=4), synonymous (n=11), and UTR (n=10) SNPs and an UTR indel across the 5 candidate genes located in the QTL region. In addition, 1-2 kb sequencing upstream of the Transcription Start Site (TSS) for BIRC5, SOCS3 and SYNGR2 uncovered 32 SNPs and 4 short indels. These novel polymorphisms and 580 SNPs on the Porcine SNP60 BeadArray were mapped to the 19 Mb scaffold using BLAT. The novel polymorphisms were genotyped on a subset of samples with extreme viral load (n=307). The highest LD between ALGA0110477 and the polymorphisms mapped on the scaffold was with a SNP from the Porcine SNP60 BeadArray (ASGA0086395, $r^2$=0.55) located 24.5 kb away followed by a group of 3 SNPs from SYNGR2 ($r^2$=0.42-0.48) including the missense polymorphism SYNGR2 p.Arg63Cys located 123.7 kb away. Using an additive linear mixed-model and a subset of samples with extreme viral load (n=307) genotyped for all polymorphisms mapped to the scaffold (n=632), we found that the SYNGR2 p.Arg63Cys and a 1 bp insertion (BIRC5 g.-343delA) located 343 bp upstream of BIRC5 TSS were associated with the largest effects on PCV2 viral load (FIG. 3)(F-ratio>47, P<0.0001). The phenotypic variance explained by each of these novel polymorphisms was substantially larger (21-23%+/−6.1-6.4%) compared to the original QTL SNP ALGA0110477 (12.6+/−4.8%). As expected, these polymorphisms were associated with large effects on all weekly viremia (P<0.0001), but also on PCV2-specific antibodies, starting from 14 dpi for IgM and 21 dpi for IgG (p<0.0001). The effects on growth during the challenge were most evident after 14 dpi as well as during the entire challenge period (0-28 dpi)(P<0.0005).

SYNGR2 a Potential Candidate Gene Influencing PCV2 Replication.

Figure 4:
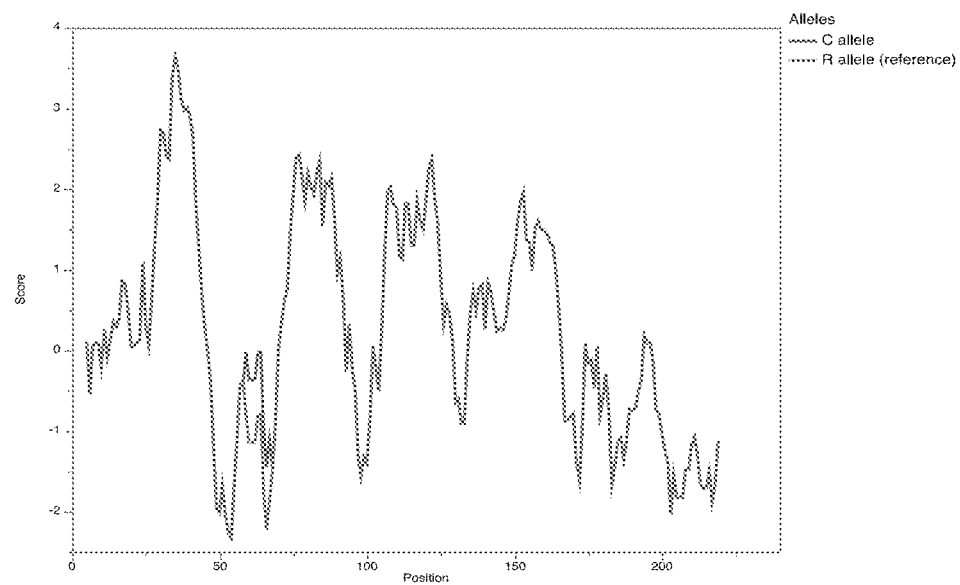
FIG. 4 is an illustration of the hydrophobicity profile of the SYNGR2 Arg63Cys polypeptides based on the Kyte and Doolittle scale (the window consisted on 9 amino acid residues). An increase in the hydrophobicity score was observed in the predicted SYNGR2 Cys63 polypeptide.

The SYNGR2 p.Arg63Cys is located in the first loop of the SYNGR2 protein in a region conserved across mammals known to be crucial for formation of microvesicle membrane fraction. The Arg residue is prevalent in other species (e.g., human, rat, cow, horse) sometimes being replaced by His (Rhesus macaque, dog), Lys (prairie vole, Chinese hamster) or Gin (mouse, golden hamster) while the Cys residue appears to be specific to swine. The substitution of Arg to Cys is characterized by a change in charge as well as hydrophobicity (FIG. 4).

The SYNGR2 p.63Cys allele is favorable with the viral load of the homozygous genotype (54.3) being lower compared to the heterozygote (67.03, P=0.005) and alternate homozygote (p63Arg, 79.54, P<0.0001). The favorable homozygous genotype was also associated with lower weekly viremia (P<0.0001), IgM (>14 dpi, P<0.0001), IgG (>21 dpi, P<0.0001) and higher growth (overall 0-28 dpi and >14 dpi, P<0.001) compared to the alternate homozygote. We hypothesize that the effects on growth and PCV2-specific antibodies are simply a result of the variation in viremia potentially modulated by SYNGR2. Expression of SYNGR2 did not differ across SYNGR2 p.Arg63Cys genotypes or time points following in vivo PCV2 challenge. No interaction (P>0.30) was detected between SYNGR2 p.Arg63Cys and the SNPs associated with the largest effects from the QTL detected on SSC7 (ALGA0039682 and ALGA0039710).

The inability to uncover the QTL located on SSC12 in (McKnite et al., 2014) was based on 1) a genetic structure with a very limited number of homozygotes for SYNGR2 p.63Cys allele (Q=1.2%) compared to Engle et al. (2015) dataset (Q=18.3%), which is less favorable for detecting associations in additive statistical models, and 2) lower ability of the ALGA0110477 to capture the low viremic effects of SYNGR2 p.63Cys. While in the Engle et al. (2015) dataset the presence of the ALGA0110477 C variant had a probability of 65% to be located on the same haplotype with SYNGR2 p.63Cys, in McKnite et al., (2014) this variant is found in similar proportions in haplotypes that carry different SYNGR2 alleles (e.g. SYNGR2 p.63Cys; P=55.9%).

The 1 bp deletion located 343 bp upstream of the TSS of BIRC5 (BIRC5 g.-343delA) was found to be in high LD ($r^2$=0.83) with SYNGR2 p.63Cys allele and as expected was associated with low viral load (P<0.0001). The deletion was predicted to affect a potential motif for NR5A2, a DNA-binding zinc finger transcription factor. However, no significant difference in expression was observed between BIRC5 genotypes across time points following in vivo PCV2 challenge (P<0.17). At 14 dpi the homozygotes for the insertion exhibited an elevated nominal expression compared to the other genotypes, but the difference was not significant (P=0.061)

Located 41.9 kb apart, the high LD observed between SYNGR2 Arg63Cys and BIRC5 g.-343delA ($r^2$=0.83) hampered the ability to distinguish their individual effects in the in vivo challenge dataset. In contrast, the LD between SYNGR2 Arg63Cys and other SYNGR2 SNPs was limited ($r^2$<0.26). Similarly, the LD between BIRC5 g.-343delA and other BIRC5 polymorphisms was also limited ($r^2$<0.16).

Viral Titer is Decreased in SYNGR2 Silenced Cells Infected with PCV2

Figure 5A:
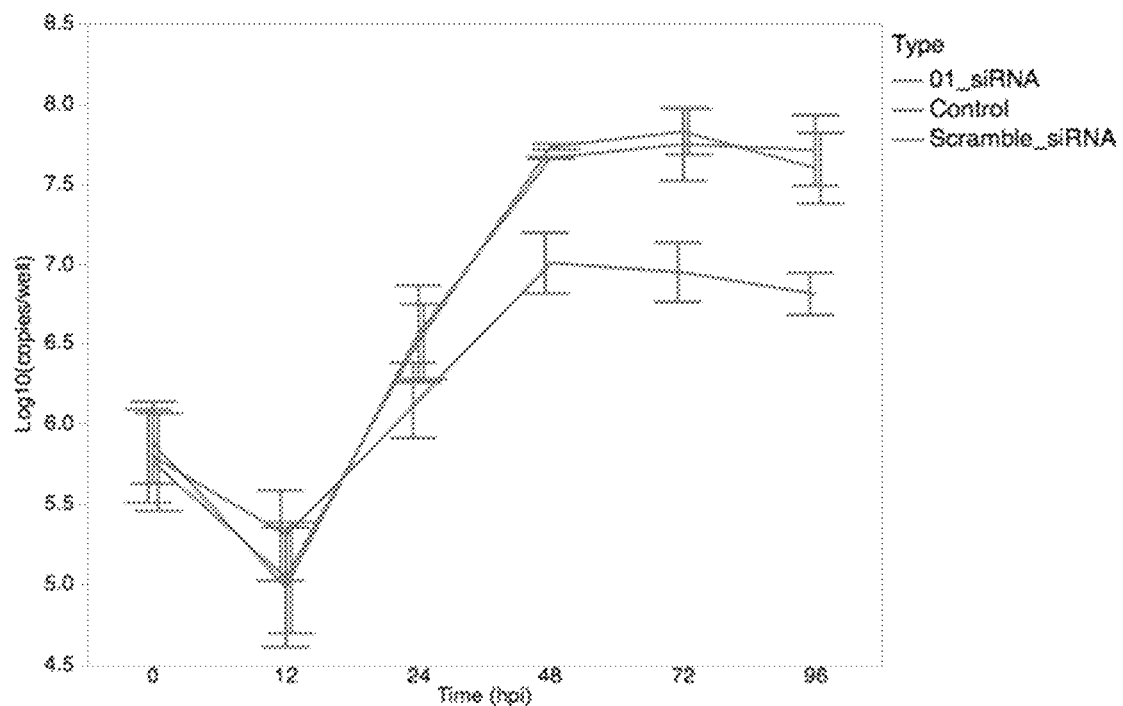
FIG. 5a is an illustration of PCV2 copy number in PK15 cells transfected with SYNGR2 specific siRNA-01, scramble siRNA and non-transfected controls following inoculation with the UNL2014001 PCV2b strain. The number of viral copies from PK15 cells is expressed as log 10 copies/well.
Figure 5B:
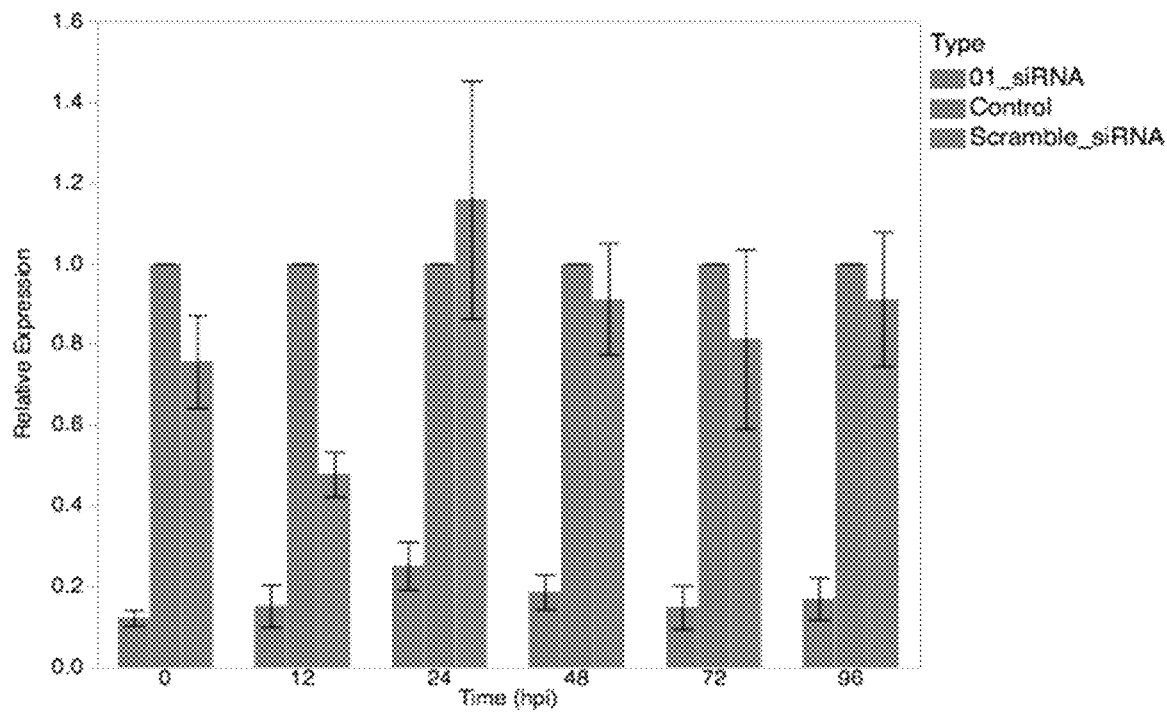
FIG. 5b is an illustration of expression of SYNGR2 in PK15 cells transfected with SYNGR2 specific siRNA-01, scramble siRNA and non-transfected controls following inoculation with the UNL2014001 PCV2b strain. Expression of SYNGR2 in siRNA-01 and scramble siRNA treated cells is presented as relative expression to the control cells.

Considering that the location of the SYNGR2 p.Arg63Cys substitution is in a conserved domain involved in vesicle formation and recent literature support of SYNGR2 affecting replication of a tick-borne human RNA virus, it was hypothesized that SYNGR2 may play a role in the internalization and early release of PCV2 from endosomes influencing its replication. In order to validate the role of SYNGR2 in promoting PCV2 replication, we transfected porcine kidney 15 cell line (PK15) with siRNA targeting the mRNA of SYNGR2. PK15 cell line has an epithelial origin and is a well-established model system for PCV2 innate immunity and cellular pathogenesis (Meerts et al., 2005). It was shown that the PK15 cells carry the SYNGR2 p.63Arg variant associated with high-viremia. Expression of SYNGR2 did not differ across time points following PCV2 infection of PK15 cells, corroborating in vivo findings. Two siRNA (siRNA-01 and siRNA-03) were evaluated at two different concentrations (10 nM and 20 nM) and found that siRNA-01 was the most efficient to knock-down mRNA level of SYNGR2 compared to the cells subjected to a scramble siRNA control. A substantial reduction (>75%) in SYNGR2 mRNA level was observed starting 24 hours after transfection (FIG. 5b). PK15 cells with the expression of SYNGR2 silenced were infected with PCV2 24 hours after transfection. A reduction in viral titer was observed in the SYNGR2 silenced cells subjected to PCV2 starting at 48 hpi when compared to scrambled siRNA and non-transfected control cells, indicating a role of SYNGR2 in promoting replication (FIGS. 5a-b).

Example 2

Materials and Methods
In Vitro Editing of SYNGR2 in PK15 Cells

Six potential guide RNAs targeting the second exon of SYNGR2 were designed and ordered (IDT), three located upstream (5') and three located downstream (3') of the SYNGR2 p.Arg63Cys polymorphism (FigSX). Each guide RNA was hybridized with fluorescently labeled Alt-R CRISPR-Cas9 tracrRNA ATTO 550 (IDT) and Alt-R S.p. Hifi Cas9 Nuclease V3 (IDT) following the manufacturer's protocol to form Ribonucleoprotein (RNP) complexes. These RNP complexes were reverse transfected into PK15 cells using Lipofectamine RNAiMAX transfection reagent (Invitrogren) at a final concentration of 10 nM. After 48 hours post transfection, genomic DNA was extracted using QIAamp Blood DNA Mini Kit (Qiagen) and amplified via PCR using LongAmp Taq DNA polymerase (NEB) with primers located in the introns flanking the second exon of SYNGR2 (5'-AGAAGGGAGAGACAGCACCA-3' (SEQ ID NO. 5), 3'-CACCAGCACATCTTCCACCT-5') (SEQ ID NO. 6). The amplicons were subjected to T7 endonuclease I (NEB) digestion following the manufacturer's protocol and visualized by agarose gel electrophoresis to assess cutting efficiency of each individual guide RNA. The ability of guide RNA pairs (upstream/downstream) to generate partial deletions of the second exon was assessed following the same RNP transfection protocol with a final RNP concentration of 20 nM (10 nM/guide RNA). After 48 hours post transfection, genomic DNA was extracted, amplified, and visualized via agarose gel electrophoresis.

A single guide RNA pair (sg31_AC/sg40_AC) was selected to generate PK15 edited clones. After 24 hours post transfection, the cells were collected and sorted using Fluorescence Activated Cell Sorting (FACS) into 96 well plates to generate single cell clones. Genomic DNA from each single cell clone was extracted using QuickExtract DNA extraction solution (Lucigen) following the manufacturer's protocol and genotyped by PCR amplification and gel electrophoresis. RNA was extracted from selected clones using All Prep DNA/RNA Mini kit (Qiagen) and PCR was performed with primers located in the 5' and 3' UTRs of the SYNGR2 mRNA sequence (5'-ACGGCGACAATG-GAGAGCGG-3' (SEQ ID NO. 7), 3'-GG-GAAACAAGAGGGGCCAGCA-5') (SEQ ID NO. 8) to amplify full-length transcripts, which were sequenced using Dideoxy sequencing. A single clone (E1_mutant) homozygous for a 107 bp deletion was plated and infected with PCV2b inoculate as previously described. Wildtype PK15 cells were concurrently infected and served as a control.

Results

PCV2b titer is significantly lower in PK15 cells that carry an edited SYNGR2 with altered protein sequence PK15 edited clones were generated using a CRISPR-Cas9 Ribonucleoprotein (RNP) complex approach with a pair of guide RNAs (31_AC/40_AC) targeting the second exon of SYNGR2 to cause a partial deletion of this exon and removal of the region containing the SYNGR2 p.Arg63Cys polymorphism. Sequencing of the mRNA from selected PK15 edited clones revealed a single clone homozygous for the same 106 bp deletion (E1_mutant). This deletion is predicted to cause a shift in the reading frame and an altered protein (189 residues) beginning at amino acid residue 42 compared to the wildtype SYNGR2 sequence (225 residues). The deleted fragment included the conserved motif located on the first loop while the shift in the reading frame affected the C-terminus of SYNGR2. A significant difference was observed in viral titer starting at 24 hpi between the wild type PK15 and the PK15 carrying an edited SYNGR2.

Discussion

Substantial variation in efficiency of viral replication and specific immune response was reported in our previous studies of experimental infections with PCV2 (McKnite et al., 2014; Engle et al., 2014). Host genotype explained a substantial proportion of the phenotypic variation for viremia, viral load and immune response, with two major QTL identified on SSC7 and SSC12. Dissection of the SSC12 QTL based on gene annotation, genomic and RNA-sequencing uncovered a non-conservative substitution in a key domain of the SYNGR2 gene associated with PCV2 viremia and immune response. Synaptogyrin-2 (SYNGR2) is a non-neural member of the synaptogyrin family, a group of genes primarily expressed in the membrane of synaptic vesicles of neuronal cells with roles in vesicle biogenesis, exocytosis and recycling via endocytosis. There is limited information about the functional role of this member of the gene family. Recently, SYNGR2 was implicated as an active player in promoting viral RNA replication and immune evasion of thrombocytopenia syndrome virus (SFTSV), a novel tick-borne bunyavirus in humans. SYNGR2 interacted with non-structural viral proteins to promote the formation of lipid-based inclusion bodies within the cytoplasm of infected cells. SYNGR2 mRNA had been upregulated more than 200-fold at 36 hpi with SFTSV. In vitro silencing of SYNGR2 resulted in a decrease in viral replication and a reduction in the number and size of the inclusion bodies, further substantiating the role of SYNGR2 in facilitating SFTSV infection.

The involvement of inclusion bodies in viral replication has also been reported in other paramyxoviruses, characterized by negative-sense single stranded RNA, such as human respiratory syncytial virus (hRSV), measles virus, and human metapneumovirus. Following PCV2 uptake, virus-like particles (VLP) were found to be integrated into intracytoplasmic inclusion bodies in infected cells, in both in vivo and in vitro experiments. The VLP are localized in endosomes at the initial phase of infection. After release from early endosomes, the viral capsid of PCV2 has been shown to induce acetylation of microtubular ca-tubulin interacting directly with dynein, a molecular motor used to transport VLPcargo along microtubules to the nucleus for replication. PCV2 is a DNA virus and replication of the viral DNA takes place in the nucleus. As a result, the involvement of SYNGR2 in endocytosis indicates its potential role in modulating PCV2 replication and disease progression. It has been suggested that after replication, PCV2 uses the Golgi complex and Rough Endoplasmic Reticulum (RER) for viral assembly and transport to the plasma membrane in a similar approach as the Bunyamwera virus, another member of the Bunyaviridae family like SFTSV.

Similarly, our study showed that silencing the expression of SYNGR2 in PK15 cells was associated with a significant reduction in PCV2 titer indicating a role of SYNGR2 in promoting viral replication. SYNGR2 p.Arg63Cys, the only missense polymorphism identified in SYNGR2 and characterized by a predicted change in charge and hydrophobicity, is located in a region conserved across mammals. In rats, the first intraluminal loop and C-terminus of SYNGR2 were found to be crucial for successful incorporation of the protein into vesicular membranes and vesicle formation. Replacement of residues 67-73 in the first loop led to protein degradation, with residues 70-73 having the largest impact. In pigs, this segment of four residues is analogous to amino acids 60-63. Because SYNGR2 p.Arg63Cys substitution is located within this crucial domain, we hypothesize that SYNGR2 p.63Cys allele affects incorporation of SYNGR2 into endosomes and efficient trafficking of VLP to the nucleus for replication.

In our research we did not observe an increase in SYNGR2 mRNA levels following in vitro or in vivo infection with PCV2. However, this may reflect important distinctions between SFTSV and PCV2. It is possible that PCV2 infection does not require an increase in SYNGR2 expression and is rather contingent on specific SYNGR2-PCV2 interactions. Because the position of this substitution is clearly located in an intraluminal loop and not part of a transmembrane region (Janz and Sudhof, 1998), an interaction between SYNGR2 and a ligand is favored compared to the potential impact of SYNGR2 p.Arg63Cys on overall protein folding or conformation of the first intraluminal loop. A shift in the position of the second transmembrane helix as a result of the substitution was predicted by HMM-TOP software (Tusnaday and Simon, 2001; (FIG. 4), but not supported by others (e.g., TMHMM, DisEMBL, PSIPRED). The substitution appears to be located in a disordered region (lacking secondary structure) that links two transmembrane helices predicted with low confidence by PSIPRED and does not appear to have any structural impact.

These results could have potential relevance across species. Polymorphisms in critical domains of human SYNGR2 (NP_004701.1) located in the first luminal loop (residues 57-63) and carboxyl terminus (residues 168-177) could influence the outcome of SFTSV infection, characterized by less specific symptoms but mainly displaying severe fever, important loss in platelets and white blood cells, and mortalities ranging from 5-15% (Sun et al., 2016). The virus was first reported in China in 2010, and since 2013 has spread to Korea and Japan. The low frequency variant of the missense polymorphism like rs201164319 (SYNGR2 p.Arg169His) found by 1000 Genomes Project (available at the international genome website) present in South and East Asia is located in the conserved segment of the C-terminus and characterized as deleterious by SIFT prediction software). Knowing the role of SYNGR2 in RNA viral replication as a result of interaction with non-structural SFTSV, we can hypothesize that variants affecting important SYNGR2 domains have the potential to affect disease outcome.

CONCLUSIONS

In this study, we integrated GWAS, RNA-seq and in vitro siRNA gene silencing and uncovered the potential role of a SYNGR2 polymorphism in promoting viral replication, immune response and growth following experimental infection with PCV2. The polymorphism, SYNGR2 p.Arg63Cys, located in a conserved region of the first intraluminal loop could influence incorporation of SYNGR2 into vesicular membranes, impact vesicle formation and efficient trafficking of the PCV2 to nucleus for replication. While further research is required to define the mechanism in which SYNGR2 and its alleles alter PCV2 replication, two theories are proposed based on current findings and the nature of PCV2 infection. We hypothesize that the interaction between a ligand and the protein encoded by the SYNGR2 p.63Cys allele may 1) compromise the ability of the virus to enter the cell through the endocytic pathway or be internalized into endosomes following cellular entry, or (2) alter capsid release from early endosomes, preventing migration of the virus to the nucleus for DNA replication. These findings will contribute to a better understanding of the critical players involved in pathogenesis of the PCV2 infected cells and also of the host genetics role in viral disease susceptibility.

What is claimed is:

1. An in vitro method of determining increased resistance to PCV2 infection in a pig cell comprising the steps of:
   (i) introducing a nucleic acid encoding a CRISPR-Cas9 into said pig cell, which introduces a single nucleotide polymorphism (SNP) in the cells SYNGR2 gene to produce the SNP SNYGR2 p.Arg63Cys into said pig cell to generate a genetically-modified pig cell comprising said SNP,
   (ii) infecting the genetically-modified cell from step (i) and a non-genetically modified pig cell with PCV2, and
   (iii) comparing the resistance of the genetically-modified pig cell from step (ii) against PCV2 infection with a non-genetically modified PCV2-infected pig cell which does not express the SNP SYNGR2 p.Arg63Cys;
   wherein a decrease in PCV2 titer in the genetically-modified cells indicates increased resistance to PCV2 infection.

2. The method of claim 1, wherein resistance to PCV2 infection in pig cells is increased by at least 10%.

3. An isolated genetically modified pig cell whose genome comprises the SNP SYNGR2 p.Arg63Cys,
   wherein the SNP is introduced via CRISPR-Cas9 editing of the pig cells SNYRG2 gene and the genetically-modified pig cell exhibits increased resistance to infection by PCV2 as compared to a non-genetically modified pig cell infected with PCV2.

4. The method of claim 1, wherein said cells are PK15 cells.

5. The genetically modified pig cell of claim 3, wherein said cell is a PK15 cell.

6. The genetically modified pig cell of claim 3, wherein resistance to PCV2 infection in the pig cell is increased by at least 10%.

* * * * *